(12) United States Patent
Holm

(10) Patent No.: US 8,772,743 B2
(45) Date of Patent: Jul. 8, 2014

(54) CONTROL METHOD FOR ELECTRON BEAM STERILIZING DEVICE AND DEVICE PERFORMING SAID METHOD

(75) Inventor: Kurt Holm, Baden (CH)

(73) Assignee: Tetra Laval Holdings & Finance S.A., Pully (CH)

( * ) Notice: Subject to any disclaimer, the term of this patent is extended or adjusted under 35 U.S.C. 154(b) by 138 days.

(21) Appl. No.: 13/122,914

(22) PCT Filed: Sep. 25, 2009

(86) PCT No.: PCT/EP2009/006942
§ 371 (c)(1),
(2), (4) Date: Apr. 6, 2011

(87) PCT Pub. No.: WO2010/040454
PCT Pub. Date: Apr. 15, 2010

(65) Prior Publication Data
US 2011/0198513 A1     Aug. 18, 2011

Related U.S. Application Data

(60) Provisional application No. 61/173,422, filed on Apr. 28, 2009.

(30) Foreign Application Priority Data

Oct. 7, 2008 (SE) ..................................... 0802102

(51) Int. Cl.
*A61N 5/00* (2006.01)
(52) U.S. Cl.
USPC ...................................................... 250/492.3
(58) Field of Classification Search
USPC ....... 250/396 R, 397, 398, 400, 492.1, 492.3, 250/306, 307, 311, 453.11, 455.11
See application file for complete search history.

(56) References Cited

U.S. PATENT DOCUMENTS 5,254,911 A * 10/1993 Avnery et al. .................. 315/366
5,378,899 A * 1/1995 Kimber ..................... 250/492.21
(Continued)

FOREIGN PATENT DOCUMENTS

JP    H01-183046 A    7/1989
JP    8-211200 A    8/1996
(Continued)

OTHER PUBLICATIONS

International Search Report (PCT/ISA/210) issued on Dec. 28, 2009, by European Patent Office as the International Searching Authority for International Application No. PCT/EP2009/006942.
(Continued)

*Primary Examiner* — Michael Logie
*Assistant Examiner* — Jason McCormack
(74) *Attorney, Agent, or Firm* — Buchanan Ingersoll & Rooney P.C.

(57) ABSTRACT

An electron beam sterilizing device, comprises: an electron-generating filament; a beam-shaper; an output window; a high-voltage supply, capable of creating a high-voltage potential between the electron-generating filament and the output window, for acceleration of electrons; a high-voltage supply for driving current through the electron-generating filament; a control unit for controlling the operation of the electron beam sterilizing device. The electron beam sterilizing device has at least three operational states which include: an OFF-state, where there is no drive current through the electron-generating filament; an ON-state, where the electron-generating filament is kept at a temperature above the emission temperature so as to generate electrons for sterilization; and a standby state, between the OFF-state and ON-state, where the electron-generating filament is kept at a predetermined temperature just below the emission temperature. The control unit controls the device to assume the standby state.

19 Claims, 5 Drawing Sheets

(56) References Cited

U.S. PATENT DOCUMENTS

| | | | |
|---|---|---|---|
| 5,396,074 A * | 3/1995 | Peck et al. | 250/453.11 |
| 5,451,794 A * | 9/1995 | McKeown et al. | 250/492.3 |
| 6,407,492 B1 * | 6/2002 | Avnery et al. | 313/420 |
| 6,949,222 B1 | 9/2005 | Möller et al. | |
| 2003/0001108 A1 * | 1/2003 | Rangwalla et al. | 250/492.3 |
| 2005/0052109 A1 | 3/2005 | Avnery | |
| 2006/0159583 A1 * | 7/2006 | Naslund et al. | 422/22 |

FOREIGN PATENT DOCUMENTS

| | | |
|---|---|---|
| JP | 9-304599 A | 11/1997 |
| JP | 2005-024343 A | 1/2005 |
| JP | 2007-010533 A | 1/2007 |
| WO | WO 01/04924 A1 | 1/2001 |
| WO | WO 2004/110868 A1 | 12/2004 |
| WO | WO 2007/095205 A2 | 8/2007 |

OTHER PUBLICATIONS

International Search Report dated Mar. 23, 2009, issued by the Swedish Patent Office in corresponding Swedish Patent Application No. 0802102-4.

English language translation of Official Action issued by Japanese Patent Office on Jan. 29, 2013 in Japanese Application No. 2011-530392 (3 pgs).

* cited by examiner

CONTROL METHOD FOR ELECTRON BEAM STERILIZING DEVICE AND DEVICE PERFORMING SAID METHOD

TECHNICAL FIELD

The present invention relates to a control method for an electron beam sterilizing device and in particular to such device adapted for sterilization of packaging laminate for packaging containers. The invention also relates to a sterilizing device using said control method.

TECHNICAL BACKGROUND

Electron beam sterilizing devices are known, which emits electrons to a web of material, such as a packaging laminate, for sterilization purposes. The level of sterilization is determined by the irradiation dose delivered onto the wall. If the delivered dose is too small the sterilization will not be adequate, and if the dose is too high the packaging laminate may be affected negatively. The negative effects include that the taste of the final product in a packaging container formed from the packaging laminate might be affected (off-taste problem) and that the packaging laminate may be deformed and/or damaged. The off-taste problem is obviously a problem to consider if the packaging laminate is to be used as a container for foodstuff, such as beverage.

The irradiation dose will be affected by, among other things, the irradiation intensity and the irradiation time. It will also be affected by the distance between the electron beam sterilizing device exit and the surface to be irradiated.

In a situation where all parameters can be varied without constraint, the problem of sterilizing packaging laminate by means of an electron beam is not a difficult task. However, in a modern foodstuff processing plant, where thousands and thousands of packaging containers are to be manufactured, sterilized, filled, and sealed in a rapid pace, the conditions are quite different. For instance, the required pace is high, and the sterilising machine thus has to operate fast.

Packaging laminate is generally provided to a filling station in large rolls of material. The rolls are unwound and led as a web to the actual location where packaging containers are formed, filled and sealed. The web of packaging laminate may be sterilized by the above electron irradiation. One immediate issue in this process is the occurrence of standstills. If no actions are taken a standstill it will result in that the same area of the web being irradiated for an overly long period of time, inevitably resulting in destruction of the material, which may lead to material failure or off-taste problems.

The general idea, as well as specific embodiments of the above is described in WO04/110868 by the present applicant.

The present invention may also be utilized in an electron beam sterilizing device for sterilisation of individual packaging containers, having an additional benefit.

SUMMARY OF THE INVENTION

It is an object of the present invention to eliminate or alleviate the above problems by providing an improved electron beam sterilizing device, and a control method for the same, in accordance with the independent claims. Preferred embodiments are defined by the dependent claims. In the following the term "beam shape" relates to the beam-intensity profile (beam profile) in a direction perpendicular to the direction of propagation.

DESCRIPTION OF EMBODIMENTS

Figure 1:
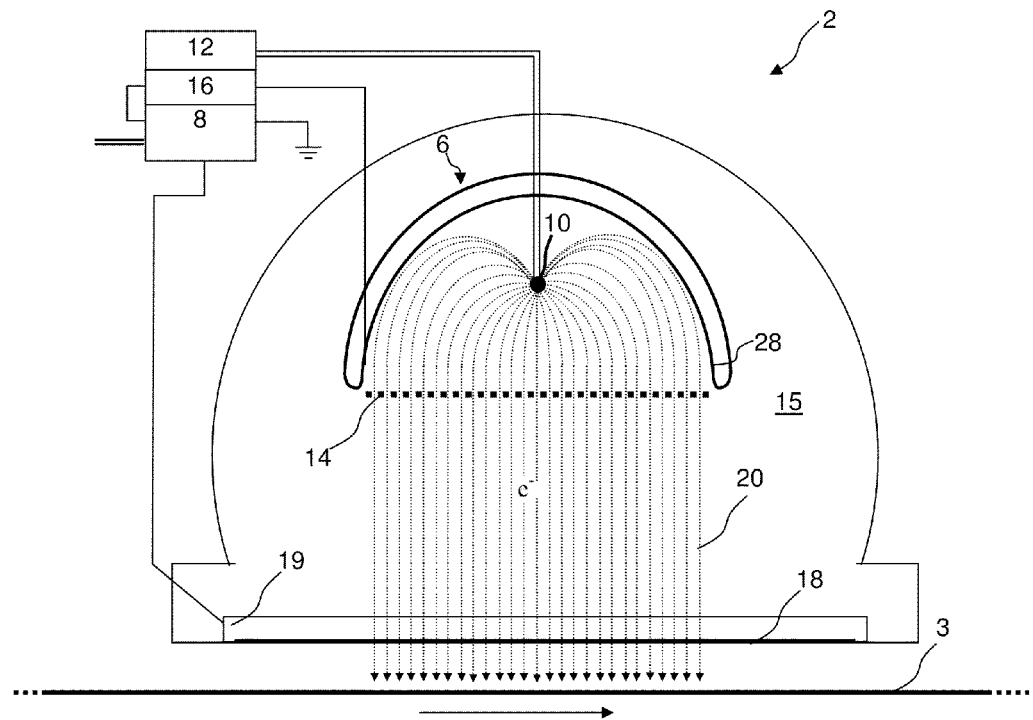
FIG. 1 is a cross sectional view in a plane perpendicular to a length direction of an electron beam sterilizing device arranged to irradiate a web of material.

A brief description of electron beam sterilization will be given in the following, referring to FIG. 1. FIG. 1 illustrates an electron beam sterilizing device 2, or emitter, arranged in register with a web of packaging laminate 3. The sterilizing device 2 basically operates as an electron gun and generally comprises an electron beam generator 6, which is coupled to a high voltage supply 8. The generator 6 has a filament 10, which is forming the free electrons, and the filament is connected to a filament power supply 12 for this purpose. The filament 10 is generally made of tungsten, and its basic function is that when it is heated to an elevated temperature, such as in the order of 2000° C., a cloud of electrons $e^-$ are emitted.

There is a grid 14 adjacent to the filament 10 and by applying or not applying a positive or negative voltage to the grid 14 by means of the grid control supply 16 the electrons formed at the filament 10 will exit the grid 14, or not. Said components are located in a vacuum chamber 15. The cathode housing 28 will act as a beam shaper, affecting the emitted electrons in a positive way. Basically, most components of the device are at least passive beam shapers in the sense that they are designed not to affect the path of the electrons negatively. For this reason reference number 28 have been used for a few more components in FIG. 2. Generally, the cathode housing and its field shaping elements serves two purposes: Firstly, the shape and in particular the radii are designed such that the field strength is not excessive and secondly the shape and geometry of the raised elements 128 are designed such that the beam profile is optimal.

It is also to be understood that the path of the electrons from the filament 10 to the exit window 18 as indicated in FIG. 1 is illustrative only, and it does not reflect real electron paths.

At the output end of the device 2 an exit window 18 is arranged, and on their way to the exit window the electrons are accelerated in a high-voltage field. The potential difference in the high-voltage field is generally below 300 kV and for the purposes of the described application it will be in the order of 70-200 kV, resulting in a kinetic energy of 70-200 keV for each electron in the electron beam 20, before passing the exit window. For other applications, however, the upper limit may be higher, and with another setup the lower limit may also be lower, and the exemplifying values should thus not be construed as limiting for the present invention. The exit window 18 is generally a metallic foil, such as titanium, having a thickness of 4-12 μm, which is supported by supporting net 19 made of aluminium or copper or any other suitable material. The supporting net prevents the foil from collapsing as a result of the vacuum inside the device. Further, the supporting net acts as a heat sink or a cooling element, such that it transports heat away from the foil. Aluminium has a tendency to degrade when subjected to the conditions during a production process, why copper is the preferred alternative for the purposes of the described application, but other alternatives are possible.

Figure 2:
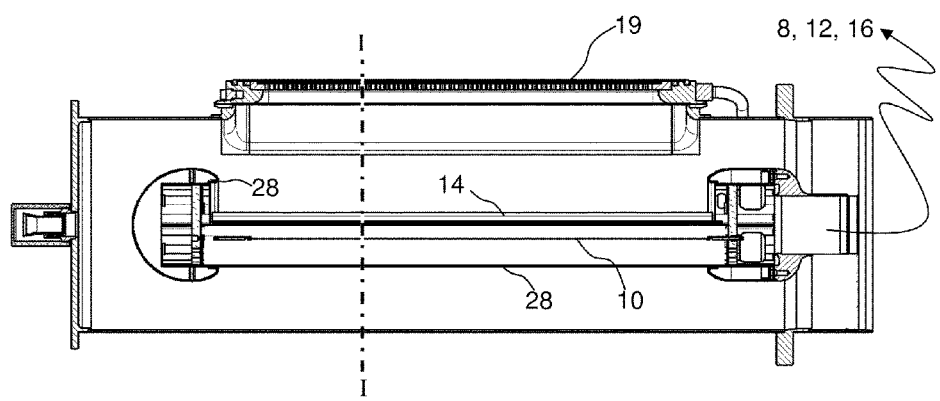
FIG. 2 is a cross sectional view in a plane parallel to a length direction of an electron beam sterilizing device according to a first embodiment of the invention, arranged to irradiate a web of material.

FIG. 2 is cross sectional view in a plane parallel to a length direction of an electron beam sterilizing device according to a first embodiment of the invention, arranged to irradiate a web of material. To facilitate understanding the same reference numbers as in FIG. 1 have been used.

Once leaving through the exit window 18 the electrons 20 will have an optimal working distance (in this case working radius) of 5-50 mm, in air at normal pressure and temperature, following a Brownian motion. Some specific examples include 5 mm for a voltage of 76 kV, and 17 mm for a voltage of 80-82 kV, with a sterilisation depth of about 10 μm in polyethylene. By altering the atmosphere in the surrounding environment around the emitter the working distance may be altered. Reducing the pressure with 50% will basically double the working distance, and exchanging the gas from air to nitrogen or helium will also affect it. Creating an oxygen-free atmosphere also results in that there will be no generation of ozone.

When sterilizing a web 3 two electron beam sterilizing devices are suggestively arranged in an aligned arrangement, "window-to-window", sterilizing opposing sides of the web. In this way a continuous sterilizing zone is created on both sides of the web 3, enabling full control of the web sterilization. Some practical aspects are discussed more thoroughly in the previously mentioned WO04/110868, by the same applicant.

Figure 3:
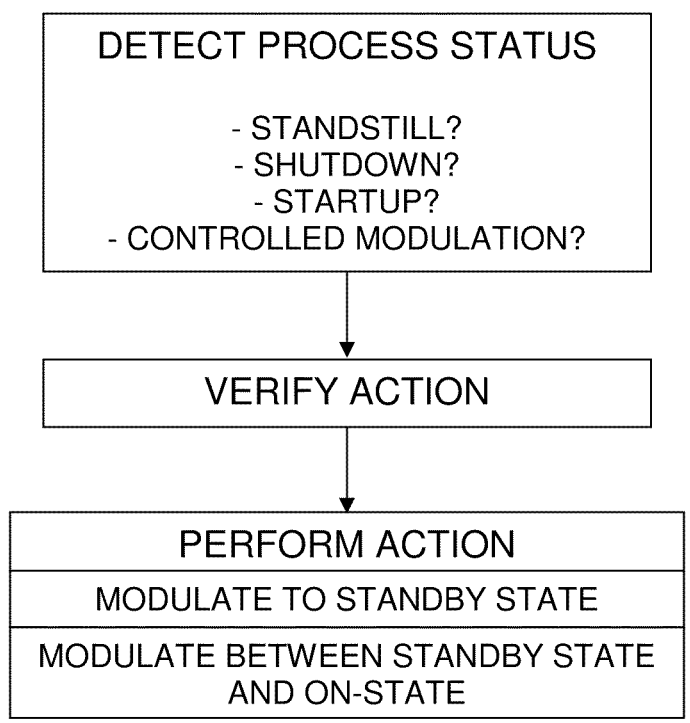
FIG. 3 is a schematic flow chart illustrating the inventive method according to a first embodiment.

According to the inventive control method the voltage of the high-voltage unit 8 coupled to the electron beam generator and controlled, so as to control the electron emission from the filament 10. Instead of cancelling the voltage completely during standstill periods, the current through the filament 10 is merely lowered to a level where there is essentially no production of electrons. By doing this several benefits are accomplished: Firstly, the emission of electrons may be controlled by the inventive method, without disrupting the voltage supply to the electron beam generator completely, or to disrupt the acceleration voltage or perform any other action to disrupt the emission of electrons during a standstill. Secondly, when the emission of electrons is to be reassumed the increase in voltage, or in filament temperature, is not dramatic, and in the order of a few 100 K rather than in the order of 1000 K. This makes the transition from no emission to emission fast. Also, the strain on the filament 10 is not as large, as it would have been. The inventive control method may also be used if the emission of electrons is to be altered rapidly, such as will be described referring to FIG. 3.

One example of the above is that a filament temperature of 2200 K results in a suitable emission of electrons, while a filament temperature of 1850 K reduces the emission to one percent of the previous value, which will be sufficient for the inventive purposes. Reductions to even lower temperatures will reduce the emission further.

This approach may beneficially be combined with grid voltage control, which will be described in connection to other embodiments, referring to FIGS. 4-10.

In the previous and following description similar components share the same last two digits in the reference numbers.

The inventive method may also be applied to a sterilization device for packaging containers, which is explained in some detail referring to FIGS. 4-10, below. This relates to a second aspect of the invention, utilizing the possibility to switching the device on and off rapidly. First some background in respect of this field of use of the invention.

Figure 4:
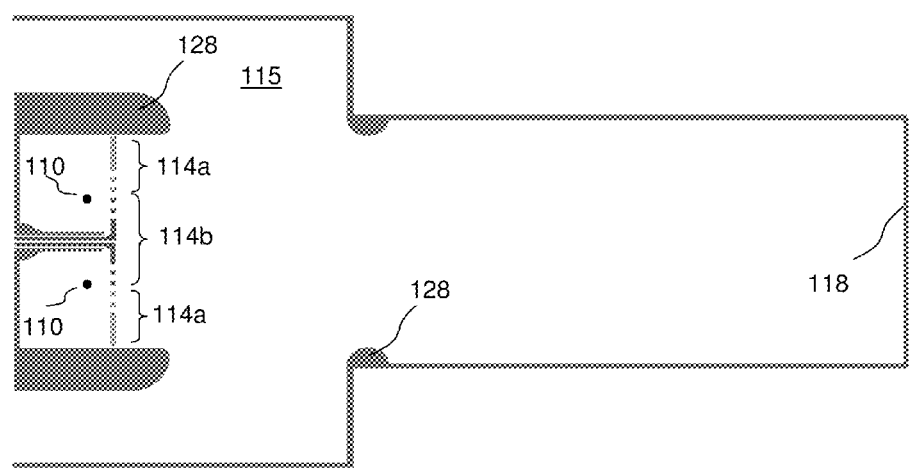
FIG. 4 is a schematic cross section of a sterilization device in accordance with a first embodiment of the present invention.

FIG. 4 illustrates an electron beam sterilizing device 102 having a construction other than the device of FIG. 1, though corresponding main components: An electron beam emitter in the form of a filament 110, a grid 114 and an acceleration space leading to an output window 118. Also shown in FIG. 4 is a "beam shaper" 128. By affecting the electric field between the filament and the window with the beam shaper 128 the electron beam can be collimated properly (or focussed/defocused). The function of the beam shaper 128 is well known in prior art and several different variants are possible. In short, the purpose of the beam shaper is to shape the field accelerating the electrons, or in another way guide the electrons in their path. The beam shaper can comprise several components arranged prior to, and along the path of the electrons. The device of FIG. 4 is adapted for insertion into an object to be sterilized, such as a ready-to-fill (RTF) packaging container, not shown.

The main difference between the device of FIG. 4 and a prior art device is that the grid 114 comprises at least two operational portions. In the illustrated embodiment there is a radially inner grid 114b (inner grid in the following) and a radially outer grid 114a (outer grid in the following). The grids 114a, 114b are individually controllable by means of a voltage. This means that a variable voltage may be applied to either one, or both of the grids 114a, 114b, in order to achieve a preferred beam configuration, e.g. a preferred beam profile.

Figure 5:
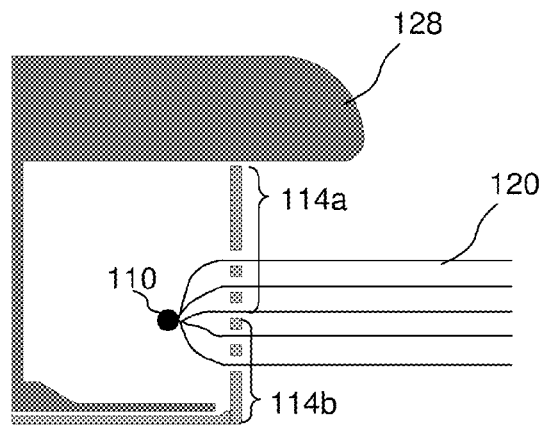
FIGS. 5-7 are partial views showing different modes of operation for a sterilization device according to a first embodiment of the present invention.
Figure 6:
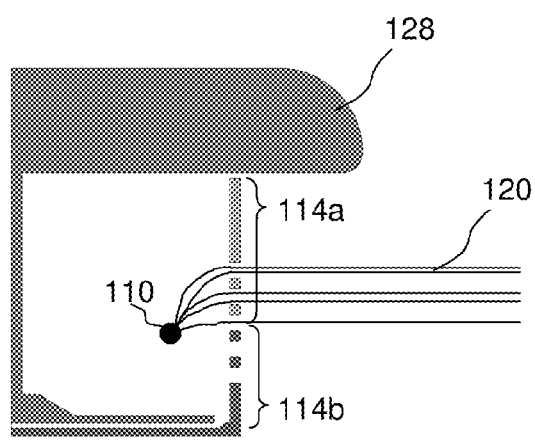
Figure 7:
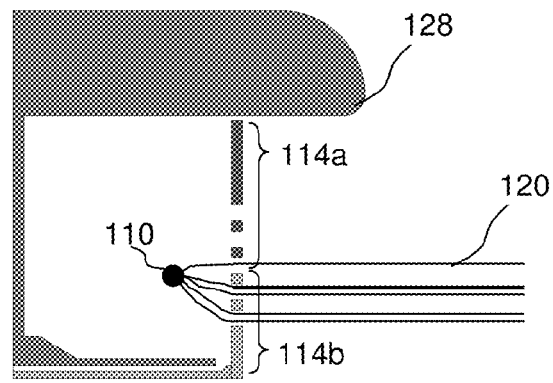

By controlling voltage applied to the inner 114b and outer grid 114a it is, in the illustrated embodiment, possible to create a small radius beam shape, by preventing electrons from passing through the outer grid 114a (see FIG. 7), an annular beam shape (doughnut-shaped profile), by preventing electrons from passing through the inner grid 114b (see FIG. 6), or a cylindrical beam shape (essentially homogenous), by allowing passage through both grids (see FIG. 5). The beam paths of the electrons are illustrated by the solid lines 120. It should be noted that the voltage applied to the grid 114a, 114b may be either positive or negative. Further, it should be noted that the voltage applied to the grid 114a, 114b is not very high, in the order of +/−100V. In the illustrated embodiment a voltage of −30-−40 V is used to efficiently block passage of electrons. For the embodiment described referring to FIG. 2 the corresponding voltage would be about −150 V. By applying a higher voltage (−80 V for the embodiment of FIG. 2) electrons may be allowed to pass the grid. This means that switching between different beam shape modes can be performed rapidly, basically as fast as the voltage can be switched, which makes the device very versatile. Further, the inventive device is space efficient, such that a high sterilization capacity may be contained in a limited space.

The grid 114 is made of any suitable electrically conductive and machinable material, generally a metal. In the illustrated embodiment stainless steel is used. The shape of the grid 114 is adapted to the desired shape of the resulting beam, and in general the grid is a metal plate equipped with holes or a wire mesh through which the electrons may pass. The solid portion of the grid 114 has the purpose of generating an electrical field with suitable properties and also has the purpose of adjusting the current from the filaments 110 by controlling the electric field strength at their surface. The holes may be circular, oblong, slit shaped, hexagonal (so as to give the grid a honeycomb shape) etc. The holes should not be so large a high electrical field gradient reaches the filament, since that would disturb the intended purpose of the grid.

Figure 8:
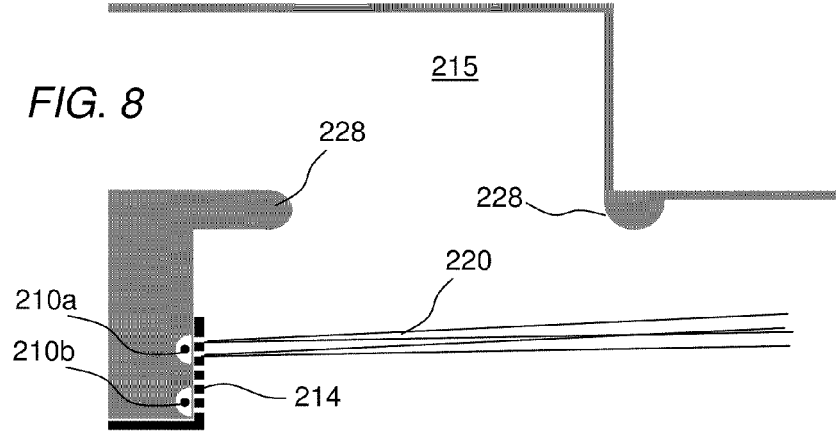
FIGS. 8-10 are partial views, similar to those of FIGS. 5-7, showing different modes of operation for a sterilization device according to a second embodiment of the present invention.
Figure 9:
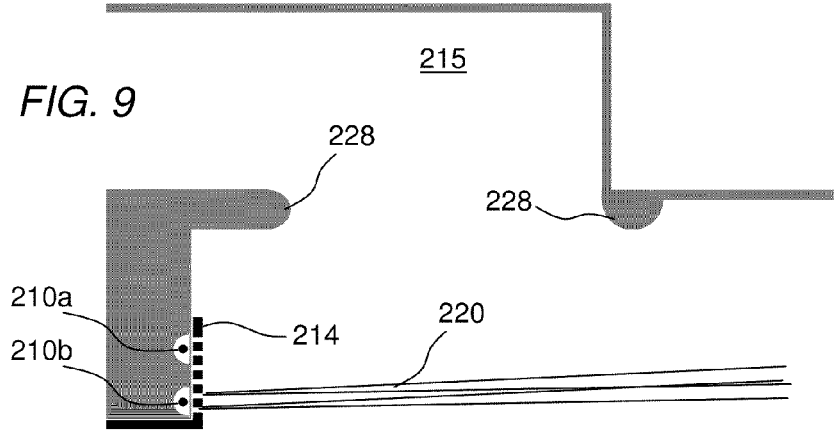
Figure 10:
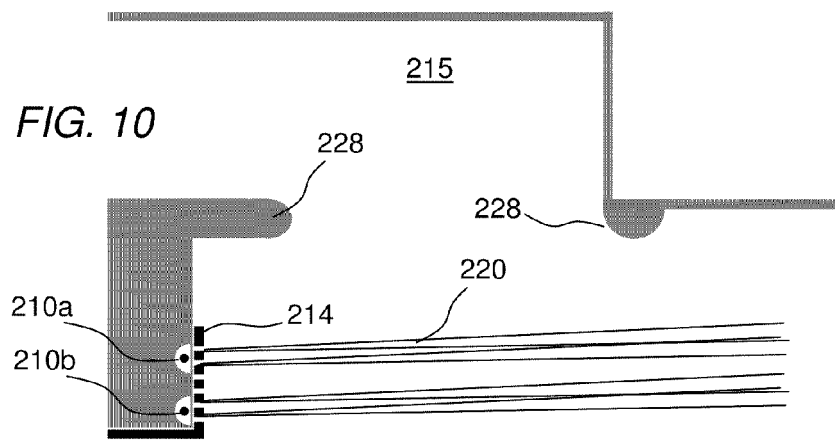

According to the inventive concept an alternative method of controlling the device is offered. FIGS. 8-10 illustrate embodiments of the device, in which the filament 210 comprises at least two, individually controllable portions, a radially inner filament 210b and a radially outer filament 210a. The figures are partial sections including the filaments 210a, b, the grid 214 and a first region of the beam path. This embodiment allows for control of the beam shape and the beam current by control of the filaments 210a, 210b, similar to what was performed with the two grids 114a, 114b of the previous embodiment. FIG. 8 illustrates how the outer filament 210a is activated for an annular beam shape, FIG. 9 how the inner filament 210b is activated for the small radius beam shape and FIG. 10 how both filaments 210a, 210b are activated for the full, cylindrical, beam shape. The beam paths of the electrons are illustrated by solid lines 220. The filaments 210a and 210b may be operated using the inventive method, such that the filaments may be switched on and of in a rapid pace and while minimizing the wear of the filaments. The input for the control of the filament may in this case be the position of the device relative to an object to be sterilized.

In another embodiment, not shown, the device of FIGS. 8-10 is altered such that the grid is removed. In this embodiment the emission of electrons is purely controlled by the control of the filaments. Other embodiments may be modified such that two filaments are used, yet only one grid covering both, or only one of the filaments.

In yet other embodiments the two previous embodiments may be combined to comprise two or more grids and two or more filaments, to achieve even better controllability.

In another embodiment the filaments may be designed, in regard of their length and diameter, in such a way that if they are connected in diameter they may be heated to optimal emission with the same current. In this case only one filament power supply is necessary. In yet another embodiment only one grid is being used. The grid has two concentric sections covering one filament each, and e.g. the outer section has a lower reach through than the inner section. Consequently, at no grid voltage both beams would be on (broad beam). With increasing negative grid voltage the outer beam would be blocked first, the inner still being active (narrow beam). Later also the inner beam would be blocked (beam off). With such an arrangement the switching and current control functions could be done with only one grid power supply.

The current control will be achieved by the filament design and filament heating current. A very fast fine tuning of the emission current can be done by controlling the grid voltage. This can be done in both cases, i.e. for the total beam and for the inner beam only.

Properties of the above described embodiments may be combined by the skilled person, and the advantage of one feature in a particular embodiment is to be understood as resulting in the same or similar advantage in another embodiment.

It should be pointed out yet again that this aspect of the invention is not limited to two filaments (or grids). The number of individually operational filaments may be varied within the physical constraints of the device in order to achieve the adequate performance of the resulting electron beam. One particular example is that a gradual shift from outer filaments to filaments could result in a more homogenous radiation of a sloping inner wall of a package, such as in a shoulder portion. The larger the sloping wall the higher the number of filaments.

In use these embodiments will be used for the same purpose and in basically the same way. The possibility of varying the beam shape rapidly makes it possible to select a suitable beam shape for various parts of the package. As the device is translated into, or out of, the package the beam shape is adjusted to sterilize the particular part of the package that the device passes. For instance, when the device passes the body portion an annular beam shape may be used, by activation of the outer grid and/or outer filament. As the device approaches the shoulder portion the beam shape is switched to a homogenous profile by activating both grids and/or filaments. For sterilization of the neck and opening device the inner grid and/or filament is used. In this way an adequate sterilization can be achieved in all locations, without overexposure.

The transition between different beam profiles can be performed very fast, such that the sterilization device can operate without affecting the flow of a production line.

It is also possible to use alternative designs for the grids and filaments, deviating from the circular symmetry illustrated in the embodiments. The designs may suitably be varied to conform to the desired beam shape, and as such vary with the shape of the package to be sterilized.

Though the technical function of an electron beam sterilization device in general is considered to be known, the function of a device in accordance with the embodiment illustrated in FIGS. 8-10 embodiment will be described in some more detail in the following.

Prior to sterilization the high-voltage field is applied. Negative voltage of about −40 V is applied to the outer and the inner grid, so as to prevent free electrons from passing through the grid. A current is led through the filament, so as to heat it to approximately 1600° C., where the production of free electrons is negligible. The device is inserted into a package to be sterilized. An alternative is to keep the device stationary, and thread the package over the device. Another alternative is to translate both the device and the package.

As the device is inserted into the package the potential of the grid is set to a higher value (which may still be negative), and the voltage applied to the outer filament is set to a level such that the temperature raises to about 2200° C. thus allowing an annular beam of electrons to be emitted from the output window so as to sterilize the inner walls of the body of the package. As the device approaches the shoulder portion of the package the potential of the outer filament returns to the stand-by state, while the voltage is applied to the inner filament, and thus the temperature of the filament, is increased, thus producing a small radius beam for sterilization of the cap portion. It should be noted that there may be an overlap so that both filaments are in an ON-state during some period of time, if necessary, e.g. in order to sterilize the tapered shoulder portion of the bottle. Both filaments may be in an ON-state during insertion of the device, producing a full cylindrical beam instead of an annular one. As the device is retracted the above process is reversed. In an alternative sterilization process the device is only active during either insertion or retraction. The above may also be used in combination with the grid-control described earlier. In this way the inventive concept may be utilized when modulating the output beam.

In use the inventive device will be arranged in an irradiation chamber, i.e. a housing protecting the surrounding environment from radiation. Packages to be sterilized are brought into the irradiation chamber in such a way that leakage of irradiation is prevented in accordance to radiation design practice. This can be achieved by means of a lock gate, the interior design of the irradiation chamber and the function therein, or by only permitting entry of packages when devices inside the irradiation chamber are not emitting electrons.

The type of package is arbitrary, but the device is particularly suited for sterilization of packages with a product contact surface (inner surface) comprising polymer. A RTF package generally comprises a body formed by a paper laminate sleeve provided with a plastic top. Yet, the device may also be used for sterilization of other products, such as medical equipment. The features of the inventive sterilization device makes it very adaptable, such that tailor-made solution for packages of various shapes is simplified, so that each area of the package may be subject to an adequate radiation dose.

The invention claimed is:

1. An electron beam sterilizing device for sterilizing packages or a packaging laminate for forming packages, the electron beam sterilizing device comprising;
    an electron-generating filament,
    a grid electrode connected to a voltage source,
    a beam-shaper,
    an output window,
    a high-voltage supply, configured to create a high-voltage potential between the electron-generating filament and the output window, for accelerating electrons to sterilize the packages or the packaging laminate,
    a high-voltage supply for driving current through the electron-generating filament,
    a control unit for controlling the operation of the electron beam sterilizing device,
    the electron beam sterilizing device having at least three operational states comprising:
        an OFF-state, where there is no drive current through the electron-generating filament,
        an ON-state, where the electron-generating filament is kept at a temperature above the emission temperature so as to generate electrons for sterilizing the packages or the packaging laminate, and
        a standby state, between the OFF-state and ON-state, where the electron-generating filament is kept at a predetermined temperature just below the emission temperature,
    wherein the control unit controls the device to assume the ON-state to generate electrons to sterilize the packages or the packaging laminate during relative movement between the output window and the packages or the packaging laminate, and controls the device to assume the standby state during a standstill of the packages or the packaging laminate being sterilized.

2. The sterilizing device of claim 1, wherein the control unit also controls the device to assume the standby state as a response to a start up procedure or as a step in a procedure of modulating the output beam.

3. The device of claim 1, wherein the difference in filament temperature between the ON-state and the standby state is less than 600 K, preferably less than 400 K.

4. The sterilizing device of claim 1, wherein the electron-generating filament and/or the grid electrode comprises at least two operational portions for variation of the current and/or profile of an output electron beam.

5. The sterilizing device of claim 2, wherein the filament and/or the grid comprises two operational portions; a radially inner portion and a radially outer portion.

6. The sterilizing device of claim 1, wherein the device is adapted for sterilization of a web of packaging laminate.

7. The sterilization device of claim 1, wherein the device is adapted to sterilize a package having a product contact surface comprising a polymer.

8. A method for operating an electron beam sterilizing device, according to claim 1, said method comprising the step of;
controlling, using the control unit, the device to assume the standby state by adjusting the current through the filament.

9. The method of claim 8, wherein the step of controlling the device to assume the standby state is executed as a response to any of the events comprised in the group consisting of:
    the standstill related to the object packages or the packaging laminate being sterilized,
    a shut down procedure being initiated,
    a start-up procedure being initiated,
    the device being operated to modulate the output electron beam between the ON-state and the standby-state.

10. The method of claim 9, wherein the step of assuming the standby state comprises the additional step of reducing a potential applied to the grid in order to prevent electrons from passing the grid.

11. An electron beam sterilizing device for sterilizing packages or a packaging laminate for forming packages, the electron beam sterilizing device comprising:
    a housing in which is located a vacuum chamber, the housing comprising an exit window;
    a filament positioned in the vacuum chamber of the housing;
    a power supply connected to the filament to drive current through the filament and generate electrons to sterilize the packages or the packaging laminate;
    a voltage supply configured to create a voltage potential between the filament and the exit window to accelerate the electrons generated by the filament, with the accelerated electrons passing out of the housing through the exit window to effect sterilization of the packages or the packaging laminate; and
    control means for controlling operation of the electron beam sterilizing device to operate the electron beam sterilizing device in at least three operational states, the three operational states comprising:
        a first state in which drive current is not delivered to the filament from the power supply;
        a second state in which drive current is delivered to the filament from the power source to maintain the filament at a temperature above an emission temperature at which the filament generates electrons; and
        a third state, between the first state and the second state, in which drive current is delivered to the filament from the power source to maintain the filament at a temperature below the emission temperature;
    wherein the control means controls the electron beam sterilizing device to operate in the third state during stand still periods.

12. The sterilizing device of claim 11, further comprising a grid positioned in the housing between the filament and the exit window, the grid being connected to a grid control supply, the grid control supply being connected to the control means which controls supply of positive and negative voltage to the grid to control emission of the electrons through the grid.

13. The sterilizing device of claim 12, wherein the grid comprises a radially inner portion and a radially outer portion, the control means being connected to the radially inner portion and the radially outer portion of the grid an separately controlling the supply of positive and negative voltage to the radially inner portion and the radially outer portion of the grid.

14. A method of controlling sterilization of a package or a packaging laminate for forming packages through use of an electron beam sterilizing device, the electron beam sterilizing device comprising a housing in which is positioned a filament connected to a power supply, the housing possessing an exit window, the method comprising:

positioning the package or the packaging laminate at the exit window while drive current, sufficient to cause the filament to generate and emit electrons, is delivered to the filament from the power supply, with the electrons generated by the filament passing through the exit window and impinging on a surface of the package or the packaging laminate as an electron beam to sterilize the surface of the package or the packaging laminate; and during a standstill, continuing to deliver drive current from the power supply to the filament but at a reduced level insufficient for the filament to generate and emit electrons.

15. The method according to claim 14, wherein the package or the packaging laminate is a web of packaging laminate, wherein the drive current sufficient to cause the filament to generate and emit electrons is delivered from the power supply while moving the web of packaging laminate past the exit window, and wherein the drive current is delivered to the filament at the reduced level when movement of the web of packaging laminate relative to the exit window is stopped.

16. The method according to claim 14, further comprising creating a voltage potential between the filament and the exit window to accelerate the electrons generated by the filament.

17. The method according to claim 14, wherein the package or the packaging laminate is a container possessing a product contact surface comprising a polymer, the product contact, surface being a surface of the container which will be contacted by food product when the container is filled with the product.

18. The method according to claim 14, wherein the drive current is delivered to the filament at the reduced level insufficient for the filament to generate and emit electrons as a response to: initiation of a shut down procedure or initiation of a start-up procedure.

19. The method according to claim 14, wherein the drive current sufficient to cause the filament to generate and emit electrons is delivered to the filament from the power supply in a first state, and the drive current insufficient for the filament to generate and emit electrons is delivered to the filament from the power supply in a second state, and wherein a difference in filament temperature between the first state and the second state is less than 600° K.

* * * * *